US00PP12719P2

(12) United States Plant Patent
Drewlow

(10) Patent No.: US PP12,719 P2
(45) Date of Patent: Jun. 25, 2002

(54) POINSETTIA PLANT NAMED 'RED ANGEL'

(75) Inventor: Lyndon W. Drewlow, Lompoc, CA (US)

(73) Assignee: Oglevee Ltd., Connellsville, PA (US)

( * ) Notice: Subject to any disclaimer, the term of this patent is extended or adjusted under 35 U.S.C. 154(b) by 0 days.

(21) Appl. No.: 09/447,598

(22) Filed: Nov. 23, 1999

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Michelle Kizilkaya
(74) *Attorney, Agent, or Firm*—Webb Ziesenheim Logdson Orkin & Hanson, P.C.

(57) ABSTRACT

A poinsettia plant named 'Red Angel' particularly characterized by the combined characteristics of an upright growth habit which permits close spacing of plants, resistance to bract fade as plant ages and under low light levels in the home and strong branch angles which minimize breakage of lateral branches during shipping.

1 Drawing Sheet

BACKGROUND OF THE NEW PLANT

The present invention comprises a new and distinct cultivar of *Euphorbia pulcherrima* known by the varietal name 'Red Angel'.

The new cultivar is a product of a planned breeding program in Lompoc, Calif. as a cross between 'Lilo Red' (U.S. Plant Pat. No. 6,694) as the seed parent and Mikkelson seedling no. 93-104-2 (unpatented) as the pollen parent. The resultant seedling was then grafted to Breeder Plant No. 94-G-71 to produce a branching plant from the original nonbranching seedling with the branching habit of Breeder Plant No. 94-G-71 and all other desirable characteristics of the original nonbranching seedling.

The following traits are determined to be basic characteristics of this new cultivar which in combination distinguish this poinsettia as new and distinct:

1. Upright growth habit which allows plants to be grown at closer spacing.
2. Resistant to bract fading as plant ages and under low light levels of the home.
3. Long lasting.
4. Strong branch angles which minimize breakage of lateral branches during shipping.

The following characteristics distinguish the new Poinsettia from other cultivated Poinsettias of this type known to the inventor. The characteristics are described with comparative reference to the cultivar 'Festival Red' (U.S. Plant Pat. No. 10,253).

1. 'Red Angel' has bracts colored a deep Red Group 45A while 'Festival Red' has bracts colored Red Group 46A to 46B.
2. 'Red Angel' has bract diameters of 23 to 28 cm while 'Festival Red' has bract diameters of 25 to 30 cm.
3. 'Red Angel' has a plant height of 27 to 30 cm while 'Festival Red' has a plant height of 30 to 33 cm.
4. 'Red Angel' has a plant spread of 35 to 40 cm while 'Festival Red' has a plant spread of 40 to 45 cm.
5. 'Red Angel' has a growth habit that is upright with very strong branch angles while 'Festival Red' has a growth habit that is semi-upright with moderate to strong branch angles.

6. Under natural short days 'Red Angel' will bloom 1 week later than 'Festival Red'. Under controlled short days both have a response time of 8 weeks.

DESCRIPTION OF THE DRAWING

The accompanying photographic drawing illustrates the new cultivar, the color being as nearly true as possible with color illustrations of this type. The photograph was taken under studio conditions seventeen weeks after rooted cuttings were planted in Lompoc, Calif.

DESCRIPTION OF THE NEW PLANT

The following detailed description sets forth the characteristics of the new cultivar. The data which defines these characteristics were collected from asexual reproductions carried out in Lompoc, Calif. The description of the plant is based on observations of a new plant propagated from the grafted plant with self-branching agent transferred. The color readings were done on a plant grown in a 15 cm pot and were taken 17 weeks after rooted cuttings were planted. Height measurements were taken from the soil line of the container. Color references are to The R.H.S. Colour Chart of The Royal Horticultural Society of London except where general terms of ordinary dictionary significance are used.

THE PLANT

Classification:
*Botanical.*—*Euphorbia pulcherrima.*
*Commercial.*—Poinsettia named 'Red Angel'.

Rooting habit: Abundant, thick, fibrous roots.

Time to root: 14 days at 21° C. in summer. 18 days at 21° C. in winter.

Type cutting: Stem tip, 5.0–6.0 cm long.

Form: Extremely upright when apical meristem is removed (pinched) leaving 5 or more nodes above the soil line. Generally, all lateral shoots develop with the lower shoots emerging first and growing longest, resulting in a canopy of bracts over the upper two-thirds of the plant.

Habit and form of growth: Strong thick stems with excellent branch angles that hold up the large bracts and reduce lateral branch breakage during shipping. Growth is vigorous. With proper growing schedules, it can be grown with no or little growth regulators.

Height: 27.0–30.0 cm.

Width: 35.0–40.0 cm.

Foliage: Leaves are alternate. Last three to four leaves before true bract are colored similar to the bracts.

FOLIAGE

Size: Mature leaves are on average 10.0–11.0 cm long and 7.0–8.0 cm wide at broadest point near the basal area of the leaf. Leaves can vary greatly depending on the location of the plant.

Shape: Ovate with acuminate tip and rounded base.

Texture:

*Upper.*—Glabrous.

*Lower.*—Glabrous and rugose because of protruding veins.

*Margin.*—Entire.

Color:

*Young foliage top side.*—Yellow-Green Group 146A.

*Young foliage under side.*—Yellow-Green Group 146B.

*Mature foliage top side.*—Darker than Yellow-Green Group 147A.

*Mature foliage under side.*—Yellow-Green Group 147B.

Leaf petiole:

*Color.*—Greyed-Purple Group 187B.

*Length.*—4.5–5.0 cm.

*Width.*—4 mm.

Veins: Pinnate, Yellow-Green Group 147B on leaf underside.

Disease resistance: Bracts have shown resistance to Botrytis and bract edge burn. No powdery mildew has been observed on leaves and bracts.

BRANCHING

Branch color: Yellow-Green Group 146A with heavy Red-Purple Group 60B cast.

Internode length: 18 mm.

Lateral stem length: 15 to 20 cm, basal is longest.

CYATHIA

Borne: Prominent on short stalks staying tightly clustered without growing apart; about 4.0–4.5 cm in diameter and 20 mm deep.

Quantity: Highly dependent on cultural conditions with 10–15 cyathia per bract on a pinched plant.

Size: Average length of 12 mm, average width of 7 mm.

Color: Yellow-Green Group 144A with reddish tip, Yellow-Green Group 146B with Red Group 46A tip at maturity.

PEDUNCLES

Length: 5 mm.

Aspect: Upright to 45° angle depending on location.

Color: Yellow-Green Group 146B.

Natural flowering season: November 17 to 20 in Lompoc, Calif.

Flower time: 8 weeks under 11 hours of daylength at 20° C. Does not heat delay at night temperatures above 23° C. Heat delay defined as the delay of flower buds initiation under short day conditions (about 10 hour day) by high night temperatures.

BRACTS

Primary:

*Length.*—12.0–13.0 cm.

*Width.*—8.0–9.0 cm.

*Margin.*—Entire.

Secondary:

*Length.*—4.5–5.0 cm.

*Width.*—2.0–2.5 cm.

*Margin.*—Entire.

Color:

*Mature.*—Between Red Groups 46A and 46B.

*Juvenile.*—Between Red Groups 46A and 46B.

*Under side.*—Red Group 53B.

Bract aspect: Flat to slightly upright.

Spread: 23.0–28.0 cm; varies depending on conditions, degree of pinching and use of growth regulators.

Number: 20–25 bracts per plant with usually 5 inflorescences per plant, but can vary depending on conditions.

REPRODUCTIVE ORGANS

Typical for poinsettia cultivars.

Stamens:

*Number.*—Numerous.

Anthers:

*Shape.*—Oblong, having an average length of 3 mm.

*Color.*—Red Group 60A.

*Filament color.*—Red Group 60A.

*Pollen.*—Abundant, yellow.

Pistils:

*Stigma.*—Shape: Forked. Color: Red Group 60A.

*Style color.*—Red Group 60A.

Ovaries:

*Number.*—3 when stigma is receptive.

*Size.*—3 mm.

*Color.*—Green-Yellow Group 144A.

Nectar cups: 2 per cyathia, Yellow-Orange Group 17A.

Post production longevity: 30 days or longer.

Presence of fruit/seeds: No seeds on plants as need to be hand pollinated to get seed set. One seed set per female flower. Many flowers are only male.

I claim:

1. A new and distinct variety of poinsettia plant as herein shown and described.

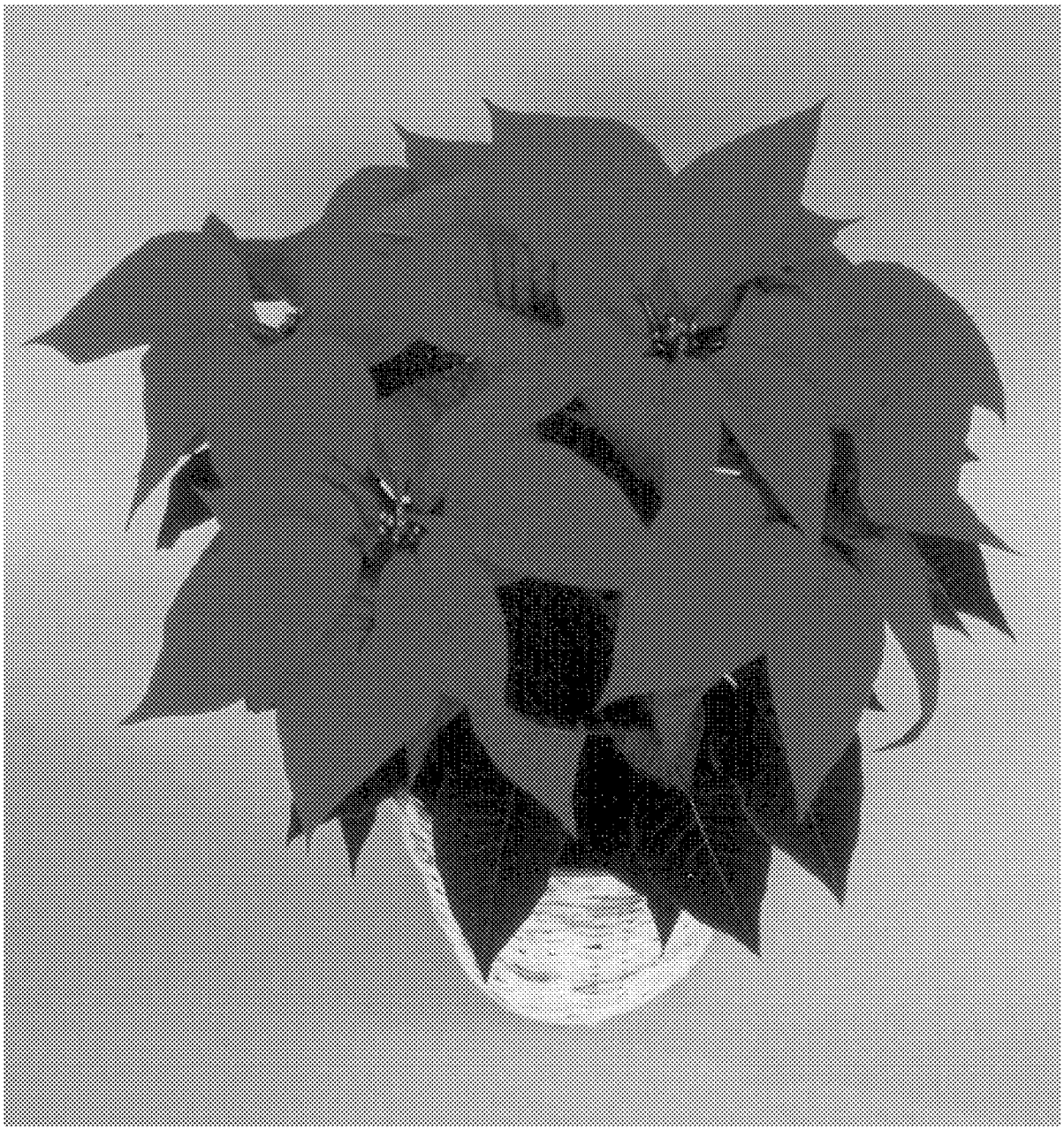

* * * * *